(12) United States Patent
Bzorgi

(10) Patent No.: US 8,850,868 B2
(45) Date of Patent: Oct. 7, 2014

(54) APPARATUS FOR SAFEGUARDING A RADIOLOGICAL SOURCE

(75) Inventor: Fariborz M. Bzorgi, Knoxville, TN (US)

(73) Assignee: Babcock & Wilcox Technical Services Y-12, LLC, Oak Ridge, TN (US)

( * ) Notice: Subject to any disclaimer, the term of this patent is extended or adjusted under 35 U.S.C. 154(b) by 435 days.

(21) Appl. No.: 13/107,525

(22) Filed: May 13, 2011

(65) Prior Publication Data

US 2012/0285220 A1 Nov. 15, 2012

(51) Int. Cl.
- *G01N 7/00* (2006.01)
- *G01R 22/06* (2006.01)
- *G08B 13/02* (2006.01)

(52) U.S. Cl.
CPC *G01N 7/00* (2013.01); *G08B 13/02* (2013.01); *G01R 22/06* (2013.01)
USPC ........... 73/31.04; 340/544; 340/541; 340/626

(58) Field of Classification Search
USPC ................................ 73/37; 340/544, 541, 626
See application file for complete search history.

(56) References Cited

U.S. PATENT DOCUMENTS

| | | | | |
|---|---|---|---|---|
| 3,948,450 | A | * | 4/1976 | Erlitz .......................... 241/46.01 |
| 3,958,313 | A | * | 5/1976 | Rossborough ............. 29/890.14 |
| 4,009,545 | A | * | 3/1977 | Rossborough ................. 408/88 |
| 4,048,813 | A | * | 9/1977 | Falk et al. ....................... 62/297 |
| 4,562,749 | A | * | 1/1986 | Clark ........................... 73/863.84 |
| 4,791,410 | A | | 12/1988 | Larsson |
| 4,908,221 | A | * | 3/1990 | Barrett ........................... 426/240 |
| 5,008,550 | A | * | 4/1991 | Barrett ....................... 250/453.11 |
| 5,406,258 | A | * | 4/1995 | Carver ........................... 340/544 |
| 5,661,474 | A | | 8/1997 | Douglas |
| 5,894,134 | A | * | 4/1999 | Kissinger ................... 250/506.1 |
| 7,186,993 | B2 | * | 3/2007 | Timpert ..................... 250/507.1 |

FOREIGN PATENT DOCUMENTS

GB 2094266 A * 9/1982 ............... G01N 1/20
WO WO 2007030740 A2 * 3/2007

OTHER PUBLICATIONS

IAEA, Gamma Irradiators for Radiation Processing, pp. 1-46, Vienna, Austria, http://www-naweb.iaea.org/napc/iachem/Brochure%20on%20gamma%20irradiators.pdf.

* cited by examiner

*Primary Examiner* — Hezron E Williams
*Assistant Examiner* — Gregory J Redmann
(74) *Attorney, Agent, or Firm* — Luedeka Neely Group, P.C.

(57) ABSTRACT

A tamper detector is provided for safeguarding a radiological source that is moved into and out of a storage location through an access porthole for storage and use. The radiological source is presumed to have an associated shipping container approved by the U.S. Nuclear Regulatory Commission for transporting the radiological source. The tamper detector typically includes a network of sealed tubing that spans at least a portion of the access porthole. There is an opening in the network of sealed tubing that is large enough for passage therethrough of the radiological source and small enough to prevent passage therethrough of the associated shipping cask. Generally a gas source connector is provided for establishing a gas pressure in the network of sealed tubing, and a pressure drop sensor is provided for detecting a drop in the gas pressure below a preset value.

4 Claims, 3 Drawing Sheets

APPARATUS FOR SAFEGUARDING A RADIOLOGICAL SOURCE

GOVERNMENT RIGHTS

The U.S. Government has rights to this invention pursuant to contract number DE-AC05-00OR22800 between the U.S. Department of Energy and Babcock & Wilcox Technical Services Y-12, LLC.

FIELD

This disclosure relates to the field of intrusion detection. More particularly, this disclosure relates to protecting radiological sources from tampering or theft.

BACKGROUND

Radiological sources are deployed in irradiation facilities for such purposes as sterilization of health care products including pharmaceuticals, deterrence of spoilage of food and agriculture products, and modification of materials such as polymers. Gamma ray emitters such as cobalt-60 and cesium-137 are popular radiological sources for such applications. The use of cesium-137 is typically limited primarily to small (desk-size) self-contained, dry-storage irradiators that are used for such applications as irradiation of blood and for insect sterilization. Cobalt-60 is typically used in large (room-size) devices for irradiating large volumes of produce and equipment. The level of radioactivity from such cobalt-60 sources is astounding, generally in a range from tens of kCi (kilo-curies) to several MCi (mega-curies). These radiological sources may be targets for malevolent actions by vandals intent upon damaging or destroying such devices, or by terrorists intent upon stealing a radiological source to make a "dirty bomb" that would create mayhem by dispersing radioactive materials in a public area. What are needed therefore are systems for protecting radiological sources from such tampering or theft.

SUMMARY

The present disclosure provides a tamper detector for safeguarding a radiological source having an associated shipping cask, where the radiological source is deployed in an irradiation facility and is accessible through an access porthole. The tamper detector typically includes a network of sealed tubing that spans at least a portion of the access porthole. There is an opening in the network of sealed tubing. The opening is large enough for passage therethrough of the radiological source and the opening is small enough to prevent passage therethrough of the associated shipping cask. The tamper detector further includes a coupling for establishing a gas pressure in the network of sealed tubing. Typically a tamper detector further includes a pressure drop sensor for detecting a drop in the gas pressure below a preset value

BRIEF DESCRIPTION OF THE DRAWINGS

Various advantages are apparent by reference to the detailed description in conjunction with the figures, wherein elements are not to scale so as to more clearly show the details, wherein like reference numbers indicate like elements throughout the several views, and wherein.

DETAILED DESCRIPTION

In the following detailed description of the preferred and other embodiments, reference is made to the accompanying drawings, which form a part hereof, and within which are shown by way of illustration the practice of specific embodiments of a tamper detector for safeguarding a radiological source having an associated shipping cask, where the radiological source is deployed in an irradiation facility and is accessible through an access porthole. It is to be understood that other embodiments may be utilized, and that structural changes may be made and processes may vary in other embodiments.

Many radiological sources, those known as panoramic sources, have a source of radiation that is stored in a pool of water when not in use. The pool of water provides radiation shielding when the radiological source is not in use. To use the radiological source it is raised out of the pool of water through an access porthole into a shielded irradiation room, which contains the materials to be sterilized. Typically the pool of water is in a storage room below the shielded irradiation room and the access porthole provides a passageway through the ceiling of the storage room and through the floor of the shielded irradiation room. Typically when such radiological sources are raised out of the pool of water into the shielded irradiation room, they emit such intense radiation that a person near the source would die within a few seconds. Consequently even a suicide terrorist would not likely be able to steal or tamper with an unshielded radiological source of this type. However, a plausible threat for such theft or tampering might be that a vandal or terrorist could lower a shielding cask over the source while it is in the pool of water, and then raise the source (covered by the shielding cask) out of the water. Such a vandal or terrorist might then be able to either vandalize the shielded source in place, by such means as a remotely controlled detonation device, or might be able to remove the radiological source from the premises in the cask for later use in a dirty bomb. Described herein are embodiments of systems for preventing such actions.

Figure 1:
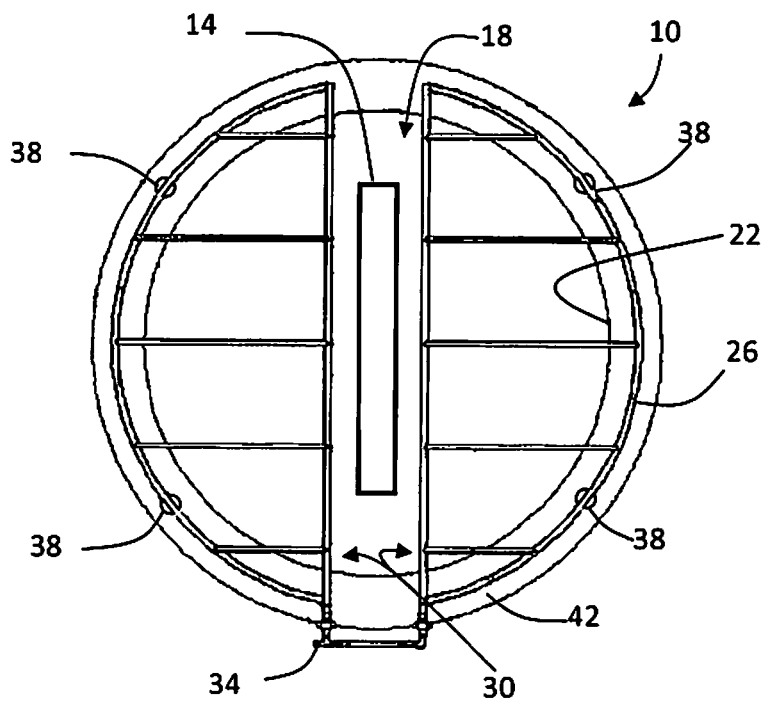
FIG. 1 is a somewhat schematic plan view of a radiological source and a network of sealed tubing spanning at least a portion of an access porthole.

FIG. 1 illustrates a tamper detector 10 for safeguarding a radiological source 14 that is disposed in a pool of water 18. The radiological source 14 is accessible through an access porthole 22. In the embodiment of FIG. 1 the access porthole 22 is circular, but in other embodiments the access porthole may be rectangular, square, or some other shape. The tamper detector 10 includes a network of sealed tubing 26. The network of sealed tubing 26 is typically formed from heavy gage material, such as 1-inch or 1½-inch Schedule 40 stainless steel pipe. The network of sealed tubing 26 is typically configured to span at least a portion of the access porthole 22, and in the embodiment of FIG. 1, the network of sealed tubing spans substantially the entirety of the access porthole 22. There is an opening 30 in the network of sealed tubing 26. The opening 30 is large enough for passage therethrough of the radiological source 14. Having an opening at least that large permits raising the radiological source 14 out of the pool of water 18 at least partially through the access porthole 22 without removing the network of sealed tubing 26 from the access porthole 22. There is a gas source connector 34 for establishing a gas pressure in the network of sealed tubing 26. Four hold-down mechanisms 38 are provided to secure the network of sealed tubing 26 to a surface 42 adjacent the access porthole 22. In various embodiments the number of hold-down mechanisms may vary depending on the shape and size of the system. In some embodiments adjustable stands may be added (or substituted for some of the hold-down mechanisms 38), to minimize any rocking motion of the network of sealed tubing 26 over the surface 42.

Figure 2:
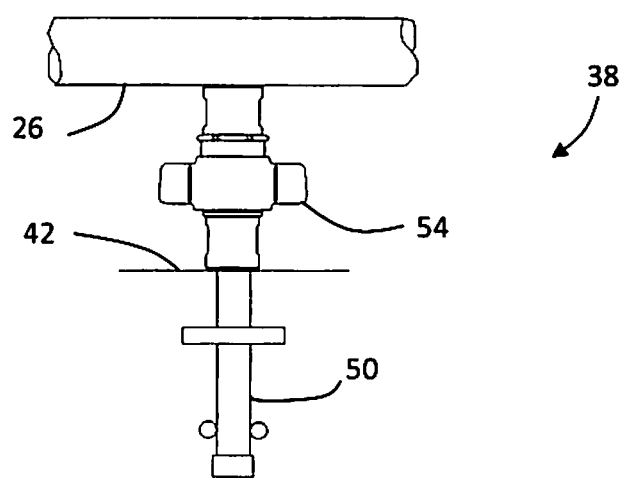
FIG. 2 is a somewhat schematic side view of an anchor and a portion of a network of sealed tubing and a coupling between the anchor and the portion of the network of sealed tubing.

FIG. 2 illustrates details of the hold-down mechanisms 38. There is an anchor 50 that is secured to the surface 42 adjacent the access porthole 22 (shown in FIG. 1). Because a plurality of hold-down mechanisms 38 are used in the tamper detector 10, there are a plurality of anchors 50 secured to the surface 42. There is a coupling 54 that is in gas communication with the network of sealed tubing 26. The coupling is secured to the anchor 50. Because a plurality of hold-down mechanisms 38 are used in the tamper detector 10, there are a plurality of couplings used in the tamper detector 10 and each separate coupling 54 is removably secured to a separate one of the anchors 50. The connections between the network of sealed tubing 26 and the anchors 50 through the couplings 54 provide secure and stable placement of the network of sealed tubing 26 around the access porthole 22. In the embodiment of FIGS. 1 and 2, the coupling 54 is a quick-disconnect device. In other embodiments each separate coupling 54 is removably secured to a separate one of the anchors 50 by a threaded connection. In some embodiments each separate coupling 54 is permanently secured to a separate one of the anchors 50 by a permanent connection such as a welded connection. However, in the embodiment of FIGS. 1 and 2 the coupling 54 is removably secured to the anchor 50. A removable connection is preferred in order that the network of sealed tubing 26 may be removed from the access porthole 22 when maintenance is needed on the radiological source 14. In the embodiment of FIGS. 1 and 2 the coupling is closed to a flow of a gas from the network of sealed tubing 26 when the coupling is secured to the anchor 50, and the coupling 54 is open to the flow of the gas from the network of sealed tubing 26 when the coupling 54 is removed from the anchor 50.

Figure 3:
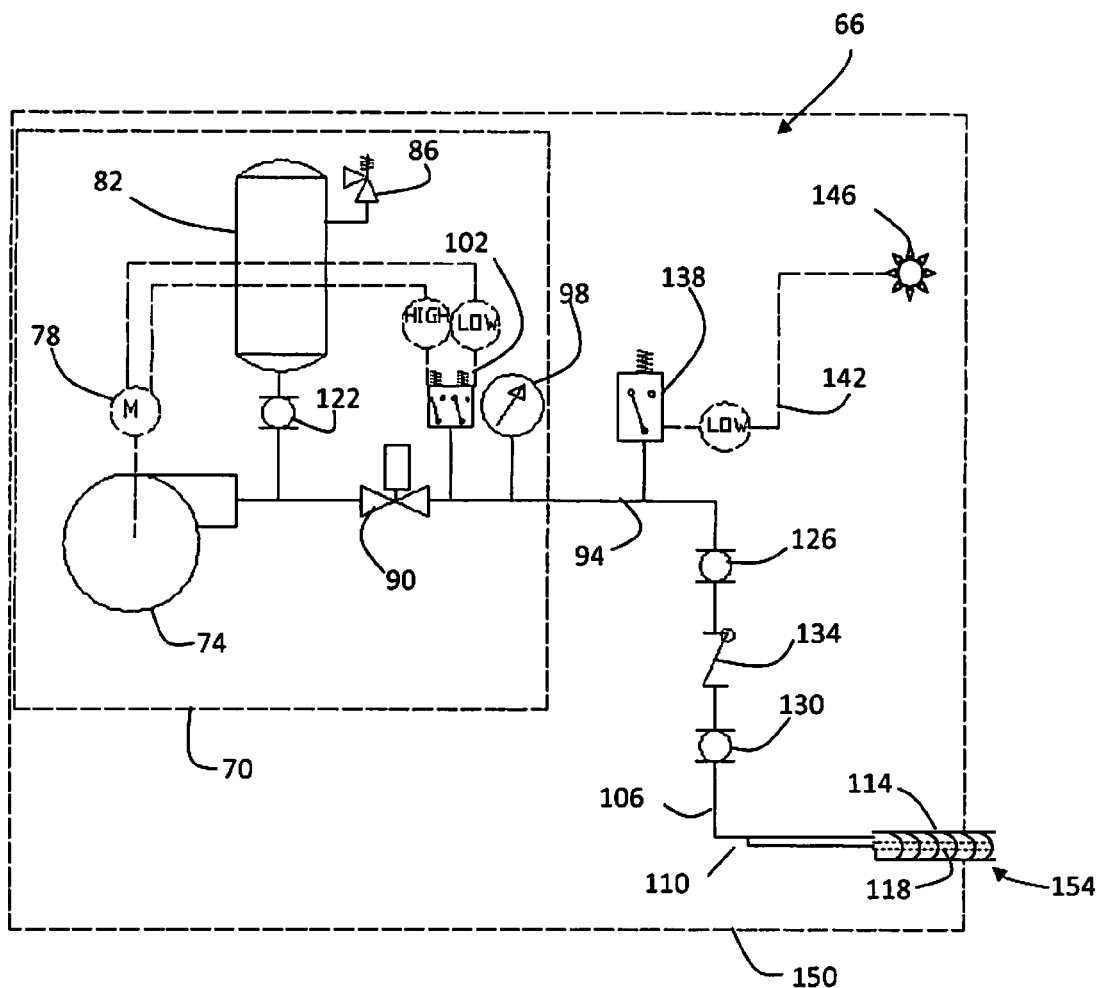
FIG. 3 is a schematic of a pressurization system for a tamper detector for safeguarding a radiological source.

FIG. 3 illustrates a pressurization system 66 for use with the network of sealed tubing 26 of FIG. 1. The pressurization system 66 includes a gas supply system 70. The gas supply system 70 includes a compressor 74 driven by a motor 78. The compressor fills a reservoir 82. The reservoir 82 has a relief valve 86 to prevent over-pressurization of the reservoir 82. A pressure regulator 90 sets a gas supply pressure for a gas supply line 94. A gage 98 is provided to measure the gas supply pressure. A pressure switch 102 turns on the motor 78 when the gas supply pressure in the gas supply line 94 drops below a low set point and the pressure switch 102 turns off the motor 78 when the gas supply pressure in the gas supply line 94 exceeds a high set point. The gas supply line 94 feeds a pressurized gas line 106. The pressurized gas line 106 is split into two parts at a tee 110. One output from the tee 110 feeds an outer tube 114 and a second output from the tee 110 feeds an inner tube 118. The pressurization system 66 further includes isolation valves 122, 126, and 130. The pressurization system 66 also includes a check valve 134, and a pressure drop sensor 138. In the embodiment of FIG. 3 the pressure drop sensor 138 is a single action pressure switch. If the pressure in the gas supply line 94 drops below a preset "low-low" value (that is lower than the low set point of the pressure switch 102), the pressure drop sensor 138 trips an electrical circuit 142 that sounds an alarm 146.

In some embodiments the isolation valve 122 is used to close off the reservoir 82 after the network of sealed tubing 26 is pressurized. This makes the system more sensitive to pressure changes in the network of sealed tubing 26 that might indicate tampering. Alternately, in some embodiments, the isolation valve 122 is left open so that gas in the reservoir 82 replenishes gas that may leak from the network of sealed tubing 26, before such leakage trips the pressure drop sensor 138 and sounds the alarm 146. The principal purpose of the check valve 134 is to prevent reverse flow of gas or debris from the network of sealed tubing 26 to the pressure drop sensor 138, which in embodiments where the pressure drop sensor 138 is a single action pressure switch, might adversely affect or damage the sensitive switches in that device. The principal purpose of the isolation valves 126 and 130 are for isolation of the check valve 134 during maintenance of the system. In some embodiments the isolation valve 130 alone may be adequate for this purpose and the isolation valve 126 may be eliminated.

The pressurization system 66 is typically contained in a protective enclosure 150. The outer tube 114 and the inner tube 118 leave the protective enclosure 150 to form a double-walled pressure detection line 154 that is connected to the gas source connector 34 (FIG. 1) of the network of sealed tubing 26. In operation the network of sealed tubing 26 is pressurized by gas from the pressurization system 66. The network of sealed tubing 26 is fabricated such that the branches being welded together externally and gas pathways through the tubing are in fluid communication. Any change in gas pressure caused by tampering with the network of sealed tubing (such as cutting, drilling, etc.) actuates the pressure drop sensor 138 and sounds the alarm 146. Furthermore, if any of the couplings 54 are disconnected from their anchor 50, then gas from the network of sealed tubing 26 is released and the alarm 146 will be activated.

When the double-walled pressure detection line 154 is connected to the gas source connector 34, the two passageways (the one through the outer tube 114 and the one through the inner tube 118 are typically interconnected to form a single supply line to the network of sealed tubing 26. As previously noted, the network of sealed tubing 26 is typically constructed from sturdy material, and such material does not generally accommodate crimping. The network of sealed tubing 26 may also be constructed from material that is also brittle and that would likely rupture if an attempt were made to crimp the tubing.

The purpose of providing a double-walled pressure detection line 154 (formed as the outer tube 114 and the inner tube 118) to the network of sealed tubing 26 is to prevent tampering with the pressure detection line 154 in a manner that would compromise the ability of the tamper detector 10 and the pressurization system 66 to detect intrusion. In particular, an intruder might try to crimp the pressure detection line 154 to seal it shut and prevent detection by the pressure drop sensor 138 of a gas pressure drop that might otherwise result from tampering with the network of sealed tubing 26. It is likely impossible to crimp a double-walled tube in a manner that would prevent gas flow (and therefore a pressure drop) through at least one of the two tubes (i.e., the outer tube 114 or the inner tube 118). The reason that it is likely impossible to prevent such gas flow is that a small gap would almost certainly remain between the outer tube 114 and the inner tube 118.

While the double-walled pressure detection line 154 would likely prevent the type of compromise described for the pressure detection line 154, the use of vacuum-grade piping might be necessary for the construction of the double-walled pressure detection line 154. However, vacuum-grade pipe may be more expensive than desired or needed in some embodiments. As an alternative, the pressure detection line 154 may be constructed as a single-walled tube with a coil spring inside. Such a structure would also likely prevent crimping of the tube in a manner that would prevent gas flow through the tube. In the embodiment of FIG. 3 a coil spring 158 is provided between the outer tube 114 and the inner tube 118. The combination of a double-walled tube and a coiled spring provides "redundant" protection against compromise of the pressure detection line. Some embodiments may employ a double-walled tube (without a coiled spring) and some embodiments may employ a single tube (only) with a coiled spring inside.

As previously noted, a plausible threat for theft of or tampering with a radiological source might be to lower a shielding cask over the source while it is in the pool of water, then raise the source (covered by the shielding cask) out of the water, and then either vandalize the enclosed radiological source in place (by remote control) or remove the radiological source from the premises in the cask. Radioactive sources are shipped in casks, and because the radioactive source decays over time (the half-life is a little over five years), spent sources must be removed from service and packaged in a shipping cask and shipped from an irradiation facility to radiological source vendor for refurbishment or disposal. Each such cask is specifically sized to accommodate a specific radiological source. Such casks are referred to herein as an "associated shipping cask." That is, an "associated shipping cask" is a cask that is associated with (i.e., specifically used for) shipping a specific radiological source. Specifically, as used herein the term "associated shipping cask" refers to the shipping cask portion of a package having a certificate that is issued by the U.S. Nuclear Regulatory Commission (NRC) to certify that the combination of the radiological source and the associated shipping cask meet the applicable safety standards set forth in Title 10 Code of Federal Regulations (CFR), Part 71, "Packaging and Transportation of Radioactive Material" and that the combination is an NRC-approved package under a 10 CFR §71.17 "General License." It is to be understood that with respect to casks and radiological sources used in governmental jurisdictions outside the United States, the radiological source and the associated shipping cask have a comparable certificate confirming compliance with comparable regulations established by that governmental jurisdiction, and such casks are encompassed by the term "associated shipping cask."

For panoramic cobalt-60 gamma-radiation sources the associated shipping casks are fabricated with lead and are very heavy, typically weighing about ten tons. Such items are expensive to ship. Consequently, the cask associated with a cobalt-60 gamma-radiation source is typically stored on-site with (or nearby) the radiological source. The availability of such a cask adds a further consideration that is addressed in various embodiments disclosed herein for tamper detectors for safeguarding a radiological source.

Figure 4:
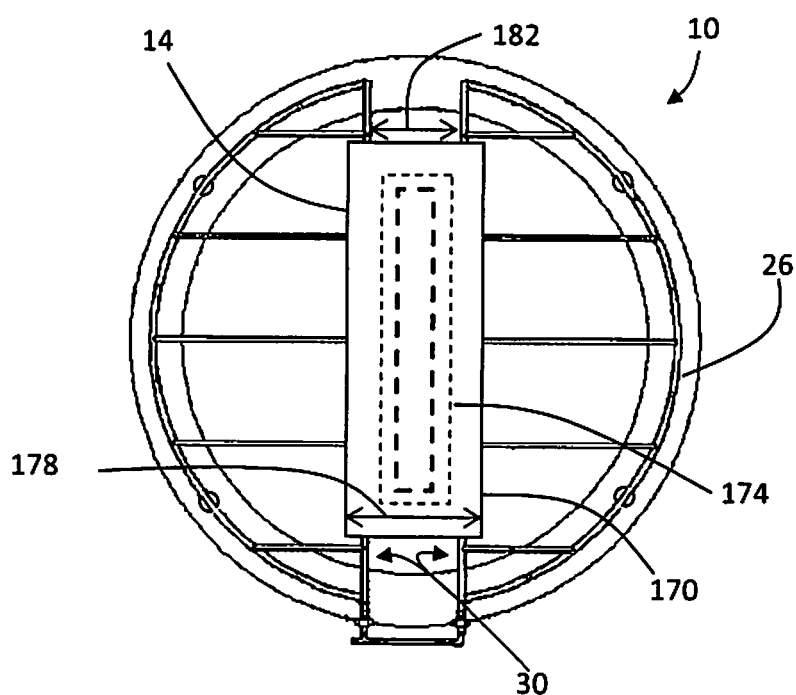
FIG. 4 is a somewhat schematic plan view of the network of sealed tubing of FIG. 1, with an associated shipping cask for the radiological source disposed over the network of sealed tubing.

As previously described with respect to FIG. 1, the tamper detector 10 has an opening 30 that is large enough for passage therethrough of the radiological source 14. Then, in order to prevent an intruder or terrorist from lowering an associated shipping cask over the radiological source while the radiological source is in the pool of water, it is desirable that the opening 30 be small enough to prevent passage therethrough of the associated shipping cask. FIG. 4 illustrates an associated shipping cask 170 for the radiological source 14. The associated shipping cask 170 has a cavity 174 that is sized to contain the radiological source 14. FIG. 4 further illustrates that the opening 30 of the tamper detector 10 is small enough to prevent passage therethrough of the associated shipping cask 170, because in the embodiment of FIG. 4 the width 178 of the shipping cask is larger than the width 182 of the opening 30 in the network of sealed tubing 26.

In summary, embodiments disclosed herein are various embodiments of a tamper detector for safeguarding a radiological source that is accessible through an access porthole. The foregoing descriptions of embodiments have been presented for purposes of illustration and exposition. They are not intended to be exhaustive or to limit the embodiments to the precise forms disclosed. Obvious modifications or variations are possible in light of the above teachings. The embodiments are chosen and described in an effort to provide the best illustrations of principles and practical applications, and to thereby enable one of ordinary skill in the art to utilize the various embodiments as described and with various modifications as are suited to the particular use contemplated. All such modifications and variations are within the scope of the appended claims when interpreted in accordance with the breadth to which they are fairly, legally, and equitably entitled.

What is claimed is:

1. A tamper detector for safeguarding a radiological source having an associated shipping cask, where the radiological source is deployed in an irradiation facility and is accessible through an access porthole, comprising:
   a network of sealed tubing spanning at least a portion of the access porthole;
   an opening in the network of sealed tubing, wherein the opening is large enough for passage therethrough of the radiological source and the opening is small enough to prevent passage therethrough of the associated shipping cask;
   a gas source connector for establishing a gas pressure in the network of sealed tubing;
   a pressure drop sensor for detecting a drop in the gas pressure below a preset value;
   a plurality of anchors secured to a surface adjacent the access porthole; and
   a plurality of couplings in fluid communication with the network of sealed tubing, each separate coupling being removably secured to a separate one of the anchors and to the network of sealed tubing such that the coupling is closed to a flow of a gas from the network of sealed tubing when the coupling is secured to the anchor and is open to the flow of the gas from the network of sealed tubing when the coupling is removed from the anchor.

2. The tamper detector of claim 1 further comprising a second pressure drop sensor for detecting a drop in the gas pressure below a preset value and activating a compressor for maintaining pressure through the network of sealed tubing.

3. The tamper detector of claim 1 wherein an alarm is sounded when the pressure drop sensor detects a drop in the gas pressure below the preset value.

4. The tamper detector of claim 3 wherein the pressure drop sensor detects a drop in the gas pressure below a second preset value for maintaining the gas pressure in the network of sealed tubing.

* * * * *